United States Patent
Seifert et al.

(10) Patent No.: US 6,652,452 B1
(45) Date of Patent: Nov. 25, 2003

(54) INFRARED ENDOSCOPE WITH SENSOR ARRAY AT THE DISTAL TIP

(75) Inventors: Gregory John Seifert, Minneapolis, MN (US); Gary David Havey, Maple Grove, MN (US)

(73) Assignee: Advanced Medical Electronics Corporation, Minneapolis, MN (US)

(*) Notice: Subject to any disclaimer, the term of this patent is extended or adjusted under 35 U.S.C. 154(b) by 319 days.

(21) Appl. No.: 09/696,398

(22) Filed: Oct. 25, 2000

Related U.S. Application Data (60) Provisional application No. 60/161,071, filed on Oct. 25, 1999.

(51) Int. Cl.⁷ .................................................. A61B 1/06
(52) U.S. Cl. ...................................................... 600/140
(58) Field of Search .......................... 60/160, 101, 178, 60/199, 245, 248, 183, 169, 555, 926; 126/922

(56) References Cited

U.S. PATENT DOCUMENTS

| | | |
|---|---|---|
| 4,868,644 A | 9/1989 | Yabe et al. |
| 4,918,521 A | 4/1990 | Yabe et al. |
| 4,919,114 A | 4/1990 | Miyazaki |
| 4,971,035 A | 11/1990 | Ito |
| 5,051,824 A | 9/1991 | Nishigaki |
| RE34,411 E | 10/1993 | Nishioka et al. |
| 5,305,736 A | 4/1994 | Ito |
| 5,445,157 A | 8/1995 | Adachi et al. |
| 5,596,992 A | 1/1997 | Haaland et al. |
| 5,634,790 A * | 6/1997 | Pathmanabhan et al. ...... 433/29 |
| 5,711,755 A | 1/1998 | Bonnell et al. |
| 5,734,418 A | 3/1998 | Danna |
| 5,749,830 A * | 5/1998 | Kaneko et al. ............. 600/160 |
| 5,827,190 A | 10/1998 | Palcic et al. |
| 5,833,596 A | 11/1998 | Bonnell et al. |
| 5,895,233 A | 4/1999 | Higashi et al. |
| 5,941,818 A | 8/1999 | Hori et al. |
| 5,944,653 A | 8/1999 | Bonnell et al. |
| 5,957,832 A * | 9/1999 | Taylor et al. ............... 600/114 |
| 5,973,844 A | 10/1999 | Burger |
| 5,977,544 A | 11/1999 | Datskos et al. |
| 6,009,340 A | 12/1999 | Hsia |
| 6,019,719 A | 2/2000 | Schulz et al. |
| 6,050,722 A | 4/2000 | Thundat et al. |
| 6,124,974 A | 9/2000 | Burger |
| 6,293,911 B1 * | 9/2001 | Imaizumi et al. ........... 600/160 |
| 6,389,306 B1 * | 5/2002 | Chaiken et al. ............. 600/474 |
| 6,428,470 B1 * | 8/2002 | Thompson .................. 600/173 |
| 6,490,490 B1 * | 12/2002 | Uchikubo et al. ........... 700/65 |
| 6,510,338 B1 * | 1/2003 | Irion et al. .................. 600/476 |

FOREIGN PATENT DOCUMENTS

| | | | |
|---|---|---|---|
| JP | 2001 286436 | * | 4/2000 |
| WO | WO 98/32380 | | 7/1998 |
| WO | WO 00/13578 | | 3/2000 |
| WO | WO 00/24310 | | 5/2000 |

OTHER PUBLICATIONS

Robinson, K., "Cantilever Thermal Detector to Challenge Microbolometer", http://www.laurin.com/Content/Mar98/techCanti.html, Mar. 1998.

Datskos, P.G., et al., "Miniature Uncooled Infrared Sensitive Detectors for in Vivo Biomedical Applications", *SPIE* vol. 3253, May 1998, pp. 94–101.

Leggett, K., "Endoscopy: Many Pluses, Still a Few Minuses", *Biophotonics International*, Mar./Apr. 1999 pp. 50–53.

Appendix B of U.S. Patent No. 6,124,974, issued Sep. 26, 2000.

* cited by examiner

*Primary Examiner*—Daniel Robinson
(74) *Attorney, Agent, or Firm*—Dicke, Billig & Czaja, PLLC (57) ABSTRACT

Endoscope apparatus and methods provide measurements of infrared radiation in the 2 to 14 micrometer wavelength range by mounting an array of infrared radiation detecting elements at the distal end of the endoscope, according to aspects of the invention. Sensor packaging techniques and elemental distributions for the sensor array provide additional advantages.

21 Claims, 9 Drawing Sheets

INFRARED ENDOSCOPE WITH SENSOR ARRAY AT THE DISTAL TIP

CROSS-REFERENCED TO RELATED APPLICATION

The subject matter of this application is related to the subject matter of U.S. Provisional Patent Application No. 60/161,071, filed Oct. 25, 1999, priority to which is claimed under 35 U.S.C. §119(e).

STATEMENT OF FEDERALLY SPONSORED RESEARCH AND DEVELOPMENT

Embodiments of the invention were made with U.S. government support under Contract No. 1 R43 CA88662-01 by the National Institutes of Health (NIH). The government has certain rights in the invention.

BACKGROUND OF THE INVENTION

1. Field of the Invention

Aspects of the invention relate to an infrared detection device including an endoscope with an array of infrared radiation detecting elements mounted at the distal end. The infrared array is sensitive at e.g. wavelengths from two to fourteen micrometers. An endoscope is a probing device used to gain access, for example visual access, to an interior cavity of a body through a relatively small hole or access channel. Examples of endoscopes used in medical applications include arthoscopes, laparoscopes, cystoscopes, bronchoscopes, etc. A preferred embodiment of the invention uses a two-dimensional array of microbolometer sensor elements packaged in an integrated vacuum package and co-located with readout electronics on the distal tip of an endoscope. An endoscope with an infrared sensing array can be used to accurately measure relative and absolute temperatures in e.g. medical, industrial, law enforcement, and other applications.

2. Description of Related Art

The electromagnetic spectrum includes ultraviolet (wavelengths from 0.1 to 0.4 micrometers), visible (from 0.4 to about 0.75 micrometers), near-infrared (From 0.75 to 1.2 micrometers), mid-infrared (from 2 to 5 micrometers) and far-infrared (from 8 to 14 micrometers). All materials at temperatures above zero degrees Kelvin emit infrared radiation. Most naturally occurring terrestrial objects have peak infrared emissions in the 8 to 14 micrometer range. Hot objects, such as jet engines, have peak infrared emissions in 3 to 5 micrometer range.

Early IR imaging systems developed in the 1970s and 1980s were unwieldy and did not lend themselves well to many applications. Physically large and technically complex, they required expensive liquid nitrogen or similar cryogenic cooling systems. IR imaging systems have been slow in delivering greater operational flexibility because of the cost, size, and weight of the cryogenic cooling components used in prior generations of high-performance IR sensors, and because of the size and power consumption of the supporting electronics.

In the early 1990s a revolutionary suite of imaging radiation sensors was developed (see U.S. Pat. Nos. RE036615, 6,114,697, 5,554,849, and 5,834,776, all of which are incorporated herein by reference). These sensors were revolutionary because they are mass-producible from materials such as low-cost silicon and they operate well at room temperatures (hence termed "uncooled").

Uncooled IR sensors, such as of the microbolometer type that Honeywell has invented, typically consist of arrays of microscopic bridge-like structures micromachined from silicon. Given the extremely low mass of the microbridge structures (typically on the order of a nanogram), they respond to very low radiation levels. Accurate measurements of microbridge temperature changes are used to quantify incident IR radiation. Common methods for measuring microbridge temperatures include the use of thin-film thermocouples to generate a thermoelectric (TE) signal, or the use of thin-film resistors that undergo resistance changes according to temperature.

The basic operating principle of an uncooled silicon IR detector is as follows. Infrared energy emitted from the target object is focused onto an extremely low mass microstructure. The incident energy is absorbed by the microstructure and causes an increase in the temperature of the bulk of the material. This temperature rise can be exactly correlated to the temperature at the optically corresponding point on the target. Honeywell's uncooled IR imaging sensors consist of arrays of microscopic (typically 0.05 mm wide and 0.001 mm thick) bridge-like structures "micromachined" into silicon wafers by photolithographic processes similar to those used to make microprocessors. Calculation of the heating of microbolometers produced by focused IR radiation can be made using the well-known physical laws of radiation, and we find that such microbolometers can measure temperature changes in a remote object with sensitivity well below 0.1 C.

For best sensitivity, microbolometer arrays should operate in an air pressure of 50 mTorr or less in the vicinity of the pixels, to eliminate thermal loss from the pixel to the air. To minimize size and weight and production costs, Honeywell has developed and patented (U.S. Pat. No. 5,895,233, incorporated herein by reference) a process allowing the completed array to be have an infrared-transparent silicon top cap hermetically attached, to form an all-silicon integrated vacuum package (IVP). This technique allows a microbolometer imaging array to have small dimensions. Existing microbolometer packages require a vacuum-sealed package around the outside of the microbolometer, resulting in larger diameters. Arrays are typically close-packed across the wafer, with a very small spacing to allow wafer sawing to separate completed arrays.

Since the sensors are fabricated using silicon photolithography, it is cost effective to fabricate large one-dimensional (1D) and two-dimensional (2D) arrays complete with monolithic silicon readout electronics if required for a particular application. Two-dimensional arrays of IR sensors may be used with an IR-transmitting lens to produce a 2D temperature map of a target, analogous to the way a visible camera produces a two-dimensional image of a target.

Other methods have also been developed to construct arrays of infrared radiation detectors, including the use of pyroelectric detector elements, p-n junction devices, microcantilevers, or photoconductive or photovoltaic bandgap materials.

Recent advances in minimally invasive surgery, for example techniques that utilize heat treatment, have resulted in a need to monitor tissue temperatures with increased accuracy. Heat treatment procedures involve, but are not limited to, the use of lasers, radio frequency (RF) devices, and ultrasonic heating methods that are typically applied using an endoscope. An example of the use of heat treatment is in the destruction of internal cancerous tumors. The challenge is to monitor the temperature of the treatment area while the heat is being applied to avoid overheating surrounding tissue and causing irreparable damage. Current methods for monitoring heat treatments include looking for visible color changes in the tissue with a visible light endoscope and the use of thermocouples on the end of an endoscope. Tissue temperatures may be monitored using infrared detectors.

The use of a visible-light imaging array on the distal end of an endoscope is well established, for example using a silicon solid-state array called a charge coupled device (CCD). Methods and devices are taught for example in U.S. Pat. Nos. 4,971,035, 5,305,736, 5,827,190, 4,918,521, 4,868,644, 5,051,824 and 6,019,719, all of which are incorporated herein by reference. U.S. Pat. No. RE035076, incorporated herein by reference, discloses that an IR filter can be used with a CCD camera on an endoscope to sense in the near-IR range. However, such a system is limited to near IR (wavelengths from 0.75 to 1.2 micrometers). The near-IR image does not have the utility for monitoring temperatures as does mid-IR and far-IR.

The prior art also has taught the construction of endoscopes capable of making IR measurements in the mid-IR and far-IR ranges. One approach is to use a series of germanium lenses (germanium is transparent to IR radiation; glass is not) in a rigid endoscope to relay IR radiation from the distal end to an external IR camera (U.S. Pat. Nos. 5,833,596, 5,711,755, and 5,944,653, all incorporated herein by reference). A second approach is taught by U.S. Pat. No. 5,445,157, incorporated herein by reference, wherein an infrared transmitting fiber of chalcogenide or fluoride glass relays IR radiation from the distal end of a flexible endoscope to an external IR camera.

Conlan et al. (WO 98/32380), incorporated herein by reference, teach a single-point articulating thoracic endoscope where the imaging assembly is a thermal imaging assembly.

The construction of infrared sensitive arrays typically requires that a vacuum surround the bolometer elements. This can be achieved using a metal package containing, for example, a germanium window and glass wire feed-thrus. Another approach, by Higashi et al in U.S. Pat. No. 5,895,233, incorporated herein by reference, teaches a method that brings together two wafers of dies that contain an infrared transparent window or top cap with either an infrared detector or emitter array to produce a low-cost vacuum package.

SUMMARY OF THE INVENTION

Aspects of the present invention provide methods for constructing an infrared sensitive endoscope to provide measurements of infrared radiation in the 2 to 14 micrometer wavelength range by mounting an array of infrared radiation detecting elements at the distal end of an endoscope. This device can be used to form a thermal image or temperature map showing the relative or absolute temperatures of an object under observation. An infrared measurement system that yields absolute temperatures is called a radiometric system. Sensor signals and electrical power are transferred from the distal tip for connection to an output device. These signals can then be manipulated and displayed visually, for example in a false-color temperature image, or used as input to a computer program for various applications.

Several different sensor technologies are envisioned for the construction of a suitable infrared radiation detecting array. Additionally, the individual sensors that make up the array can be organized in different patterns and in different numbers to achieve varying observational objectives. Additionally, the plane of the array may be situated at any angle with respect to the axis of the endoscope. The array of infrared radiation detecting elements can be used in combination with a conventional visible endoscope to provide visible and infrared information, for example simultaneous spatially aligned infrared and visible information.

An infrared transparent gas, for example carbon dioxide, flowing down a channel in the endoscope, can vent on to the outer window of the infrared array/optics assembly to remove any condensation or liquids that may collect during use. The infrared radiation detection array may include a temperature stabilization apparatus, for example a thermoelectric plate, to increase the accuracy and dynamic performance of the array. The infrared detectors may also be constructed using an integrated vacuum package. The use of three-dimensional hybrid package techniques for connecting the signals from a IR sensitive array to conditioning electronics and cabling behind the array can be used to achieve the diameter practical for an endoscope.

Aspects of the present invention use an array of infrared radiation detecting elements at the distal end of an endoscope. The array of infrared detecting elements can detect radiation in the 2 to 14 $\mu$m wavelength band (mid and far IR, according to one embodiment, as opposed to "near IR" which extends from 0.75 to 2 $\mu$m. The near-IR band can be achieved with an IR filter and a silicon CCD (visible light) camera, according to one example.

The array of the infrared detecting elements can be used with or without cooling.

Suitable types of infrared detectors include:

An infrared array made of microbridges, with the temperature of each microbridge individually sensed. These are called microbolometers.

Methods for sensing microbridge temperatures include:

Using thin-film thermocouples on each microbridge to generate a thermoelectric (TE) signal. This is known as a TE sensor.

Using thin-film resistors on each microbridge whose resistance changes with temperature.

Using a selected forward-biased p-n junction, on each microbridge.

An infrared array where the infrared detector element is a pyroelectric element.

An infrared array where the infrared detector element is a thin film diode transistor coated with infrared absorbent material, and mounted on a thermally insulating support such as silicon oxide, foam glass or foam plastics material.

An infrared array where the array elements are a resonant optical cavity.

An infrared array where the array elements are a periodic pattern of photoconductive or photovoltaic, bandgap detector elements spaced apart at a period which is equal to or less than the wavelength of IR radiation.

An infrared array where the array elements are microcantilevers.

Methods for providing a vacuum in which the infrared elements operate include:

Packaging the array elements using an integrated vacuum seal on the surface of the die to achieve a diameter practical for an endoscope.

Packaging the array elements inside vacuum-sealed capsule that uses the optical element and interconnect feed thrus as the points of the vacuum seal.

Methods for constructing the infrared array on a semiconductor die include:
- Constructing the array of infrared radiation detecting elements from silicon or GaAs material
- Constructing the array of infrared radiation detecting elements co-located with integrated silicon or GaAs circuitry.

The number and organization of infrared detecting elements on the array can be unique to each application; possible configurations include:
- Organizing the array as a linear array of one by N infrared detecting elements where N is any whole number including 1.
- Organizing the array of infrared detecting elements as a two dimensional array of N by M were N and M are any positive integer including one.
- Organizing the array of infrared detecting elements in an irregular pattern to allow it to compensate for the distortions caused by constraints on the optics.
- Organizing the array of infrared detecting elements in a circular pattern.
- Varying the density of the array elements in any pattern to provide differing levels of radiation sensing detail, for example to provide more detailed temperature mapping at critical points under observation.

The infrared detecting array can have varying orientations with respect to the central axis of the endoscope. Such orientations include:
- Mounting the array of infrared detecting elements in a plane perpendicular to the longitudinal axis of the endoscope.
- Mounting the array of the infrared detecting elements in a plane at any angle with respect to the longitudinal axis of the endoscope.
- Greater resolution can be achieved by having the array of the infrared detecting elements at an angle to the distal end of the endoscope.

Three-dimensional hybrid construction techniques can be used to assemble the distal infrared sensor assembly.

The array of the infrared detecting elements can be used to make radiometric temperature measurements. Techniques to facilitate radiometric measurements include:
- Control the temperature of the array of the infrared detecting elements using for example:
  - Control the temperature of the array of the infrared detecting elements with a thermoelectric device.
  - Control the temperature of the array of the infrared detecting element with a flow of a gas near the array.
- Monitor the temperature around the array of the infrared detecting elements.
- Insert an object(s) of known temperature in front of the array of the infrared detecting elements.

The optics used in front of the infrared radiation detection array are IR transmitting materials such as chalcogenide glass, fluoride glass, zinc selenide glass, germanium, or silicon.

The endoscope using the array of the infrared detecting elements at the distal end can be rigid or of a flexible type.

The array of infrared radiation detecting elements at the distal end of the endoscope can be collocated with a separate visible light endoscope technique such as a CCD array.

Blowing an IR transparent gas onto the lens of the IR endoscope will help prevent condensation and keep the lens free from debris that could absorb the IR radiation.

Other features and advantages according to the invention will be apparent from the remainder of this application.

DETAILED DESCRIPTION OF PREFERRED EMBODIMENTS

Figure 1:
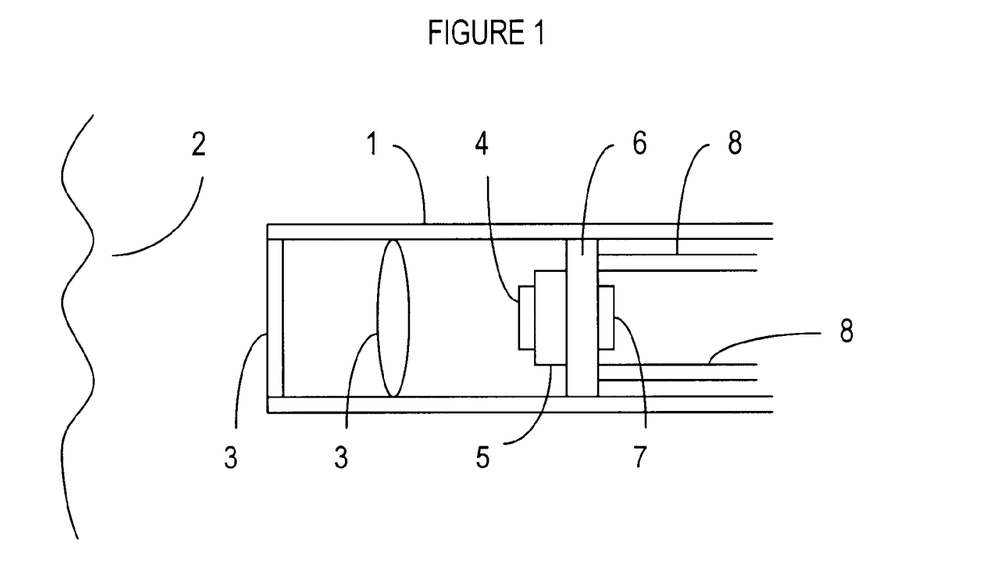
FIG. 1 shows the distal end of an endoscope with an array of infrared radiation detecting elements mounted in a plane perpendicular to the axis of the endoscope, according to an embodiment of the invention.

Aspects of the present invention relate to the use of an array of infrared radiation detecting elements mounted at the distal end of an endoscope. Referring to FIG. 1, an endoscope 1 is observing an object 2. The objective lens and window assembly 3 is used to form an infrared image of the object 2 on the array of infrared radiation detecting elements 5. The objective lens and window assembly 3 is constructed with an IR transparent material, for example chalcogenide glass, fluoride glass, zinc selenide glass, germanium, silicon, etc. To contain a vacuum over the IR detecting elements, an IR transparent window 4 is bonded to the array to form a vacuum seal. The array of IR detecting elements is mounted to an interconnect assembly 6 that connects, if necessary, to array readout electronics 7 and to interconnections 8, for example wires, that lead to the non-distal end of the endoscope.

Figure 2:
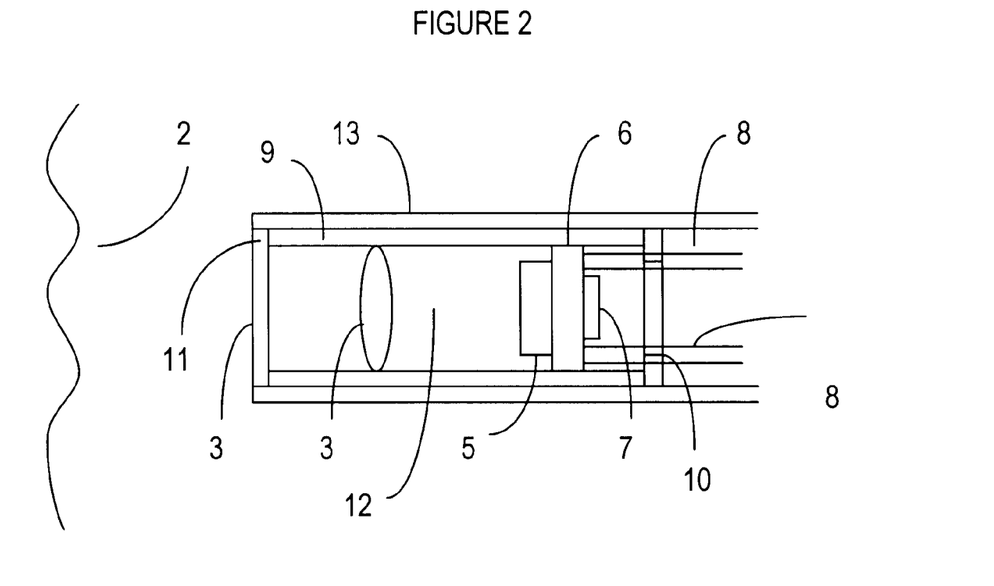
FIG. 2 shows a vacuum-sealed capsule at the distal tip of an endoscope with the array of infrared radiation detecting elements in the vacuum, according to an embodiment of the invention.
Figure 3:
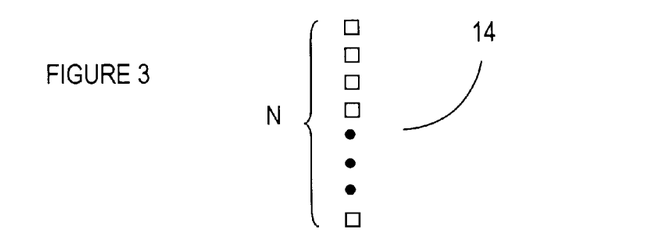
FIG. 3 shows a one-dimensional N×1 elemental organization of the array of infrared radiation detecting elements, according to an embodiment of the invention.
Figure 4:
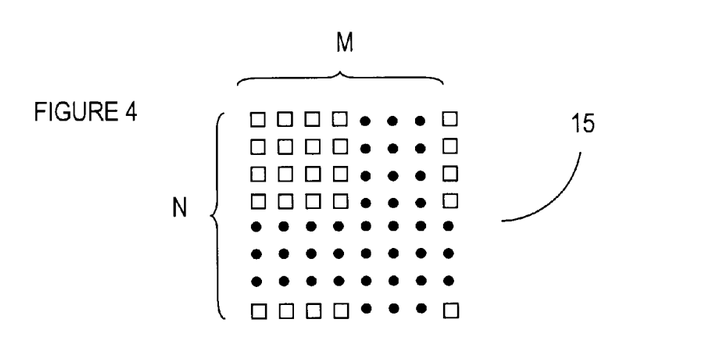
FIG. 4 shows a two-dimensional N×M elemental organization of the array of infrared radiation detecting elements, according to an embodiment of the invention.
Figure 5:
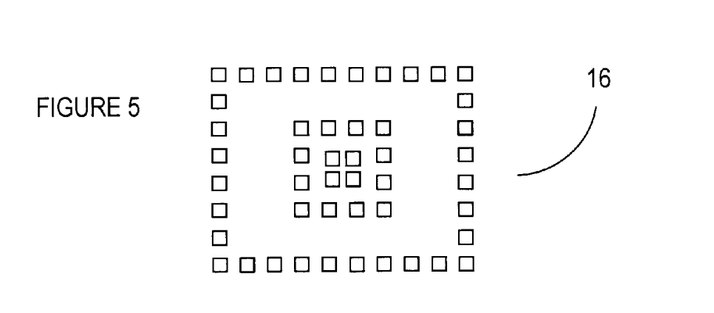
FIG. 5 shows an arbitrary elemental organization of the array of infrared radiation detecting elements, according to an embodiment of the invention.
Figure 6:
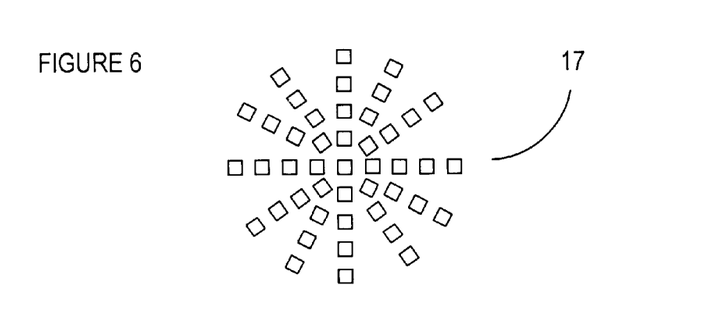
FIG. 6 shows a circular elemental organization of the array of infrared radiation detecting elements, according to an embodiment of the invention.

As an alternative to having an IR transparent window 4 over the array of infrared radiation detecting elements 5, the complete assembly can be sealed in a vacuum. In FIG. 2 a hermetically sealed capsule 9 is mounted on the distal end of an endoscope 13. The inside of the capsule 9 is at a vacuum 12. The array of infrared radiation detecting elements 5 is exposed to the vacuum. The interconnection assembly 6 has leads connecting to hermetic feed troughs on the capsule 9. These leads then connect to interconnections 8 that lead from the distal end of the endoscope. The objective lens and window assembly 3 make a hermetic seal 11 with the capsule 9. There are various ways the detecting elements in the array can be organized. FIG. 3, FIG. 4, FIG. 5, and FIG. 6 show some of these. FIG. 3 shows the detectors can be in a one-dimensional array 14 with dimensions of one by N, where N can equal one. This allows the endoscope to be for example automatically or manually rotated or swept side to side to obtain a complete temperature map of an object. The array can alternatively be a two dimensional array 15 of varying grid density with dimensions N by M, FIG. 4. Varying grid densities can be used to provide varying spatial resolution of the temperature distribution of an observed object. Such an arrangement is a staring configuration, where a temperature map of the object can be viewed constantly without moving the endoscope or its associated optical components. The array can be in irregular 16 (FIG. 5) or in circular 17 patterns (FIG. 6) to adapt to distortions caused by the optics or allow for unique concentrations of the elements.

Figure 7:
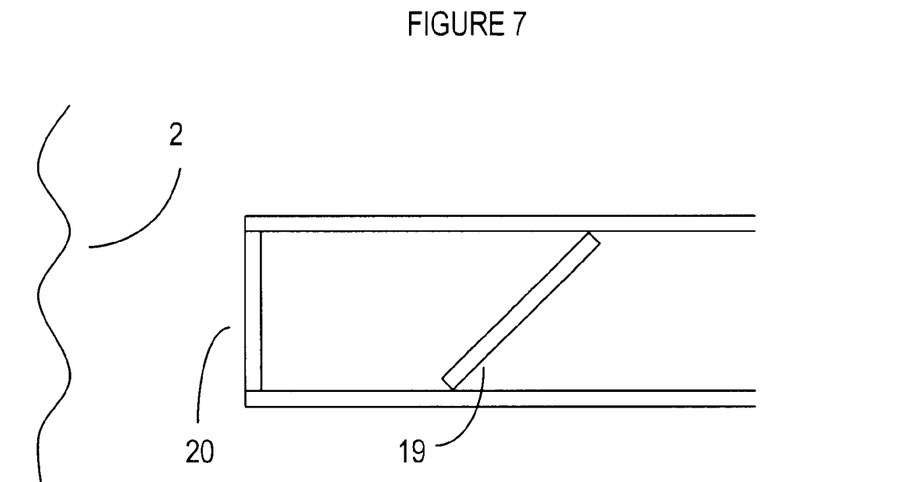
FIG. 7 shows that the infrared array can be angled in relation to the axis of the endoscope, according to an embodiment of the invention.

FIG. 7 shows that the array of infrared radiation detecting elements 19 can be at an angle to the average axis of the endoscope 20. This allows, for example, the use of a physically large array size within the constraining diameter of an endoscope.

Figure 8:
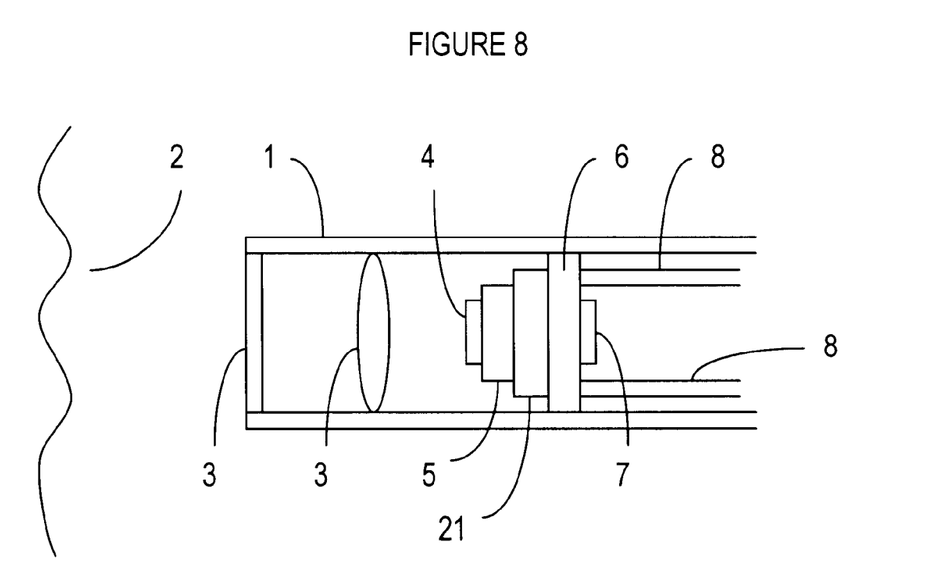
FIG. 8 shows the use of a thermal stabilization unit for improving the accuracy of radiometric measurements using the array of infrared radiation detecting elements at the distal end of an endoscope, according to an embodiment of the invention.
Figure 9:
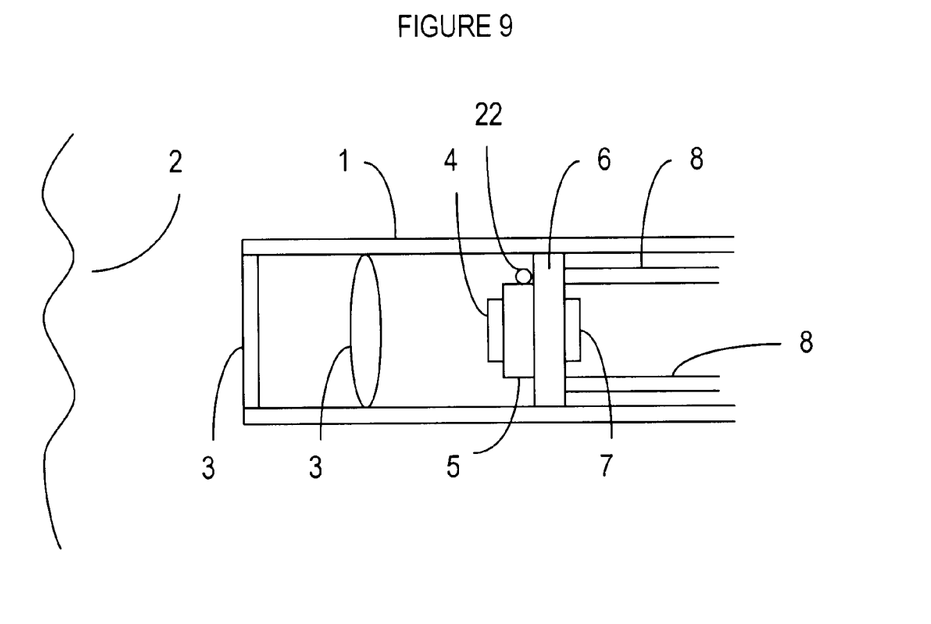
FIG. 9 shows the use of a temperature sensor for improving the accuracy of radiometric measurements using the array of infrared radiation detecting elements at the distal end of an endoscope, according to an embodiment of the invention.
Figure 10:
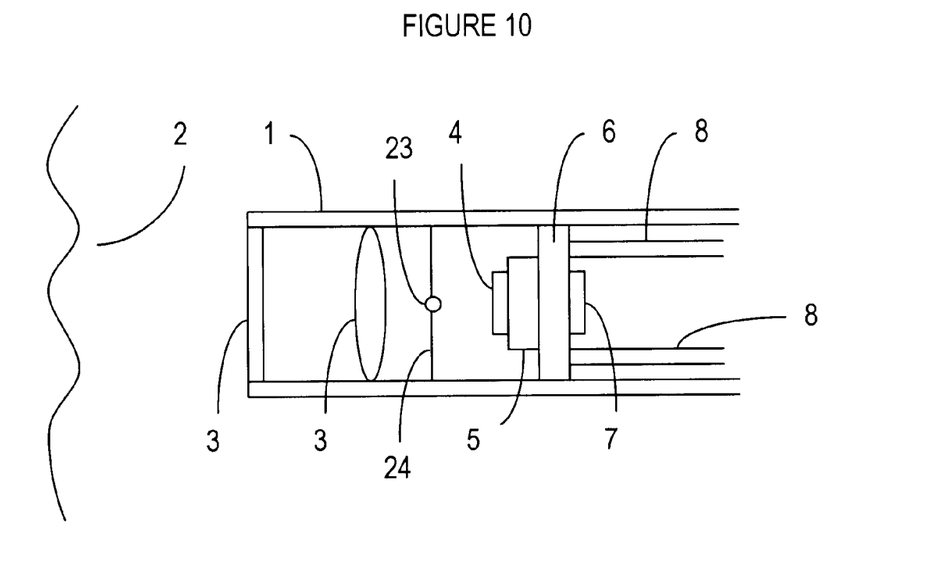
FIG. 10 shows the use of an infrared target source for improving the accuracy of radiometric measurements using the array of infrared radiation detecting elements at the distal end of an endoscope, according to an embodiment of the invention.

In many applications, it is desirable to make radiometric measurements with the array of infrared radiation detecting elements at the distal end of the endoscope. FIG. 8, FIG. 9, and FIG. 10 illustrate methods for improving the accuracy of the radiometric measurement. These methods can be used singularly or in any combination. The thermoelectric device 21 can be used to control the temperature of the array 5. The interconnect assembly 6 can be used as a thermal sink for the thermoelectric device, or conduct heat to the outer endoscope assembly 1. A temperature sensor 22 can be used to monitor the array temperature. The temperature sensor can be on the array 5 itself or on the interconnection assembly 6. Knowing the array temperature can help to compensate for the variations in the readings. A heating element 23 can be suspended in front of the array 5. The heating element 23 can be held in place with for example fine wires 24 that allow current to flow in and through the heating element 23. The temperature of the heating element can be calibrated to the amount of the current flow. The array 5 would sense the heating element 23 to provide calibration points. Several heating elements, at the same or different temperatures, may be employed. The heating element could only be energized during calibration procedures.

Figure 11:
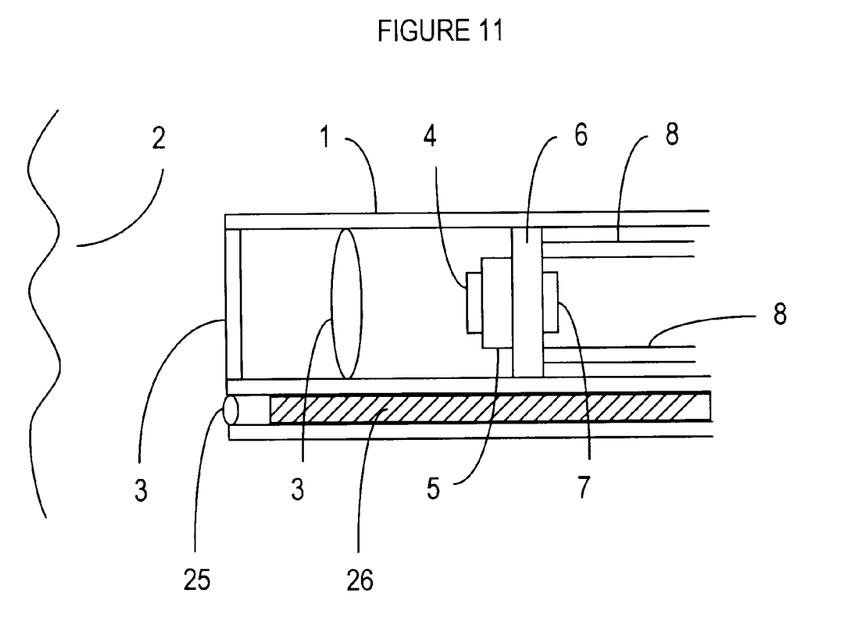
FIG. 11 shows the combination of visible light imaging and infrared radiation detection in an endoscope, according to an embodiment of the invention.

FIG. 11 shows that an array of infrared radiation detecting elements at the distal end of an endoscope can be combined with conventional visible light endoscope techniques to form both an IR and visible light imaging endoscope. The optics 25 for the visible light endoscope often need to be separate from the IR optics since the IR optics typically do not efficiently pass visible light. A conventional endoscope optical fiber 26 can be used to relay the visible light image out of the endoscope. A CCD visible imaging array could also be used at the distal end for the visible light image.

Figure 12:
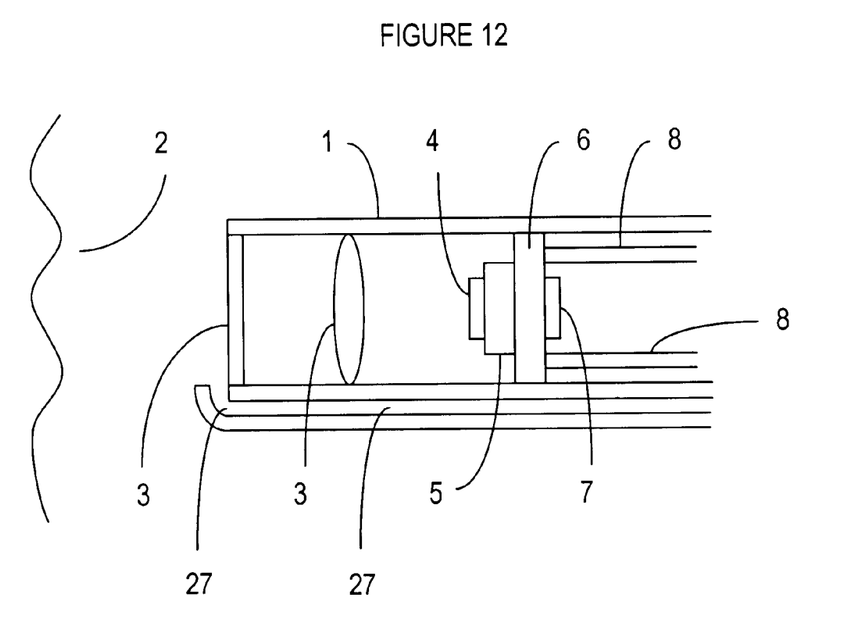
FIG. 12 shows the use of a gas flowing in a channel of the endoscope to blow liquids, condensation, and/or other debris off the infrared sensor array assembly at the distal end of endoscope, according to an embodiment of the invention.

Infrared opaque liquids, such as water, condensation and other contamination of material can collect on the outer window of the infrared array. These and other debris can absorb the infrared radiation. FIG. 12 illustrates a system for maintaining a clear path to the objective, where a channel 27 for infrared transparent gas, for example dry carbon dioxide gas, is designed into the endoscope. This gas is vented on to or across the window 3. The gas clears the window of solids, liquids, or condensation, or the like.

Figure 13:
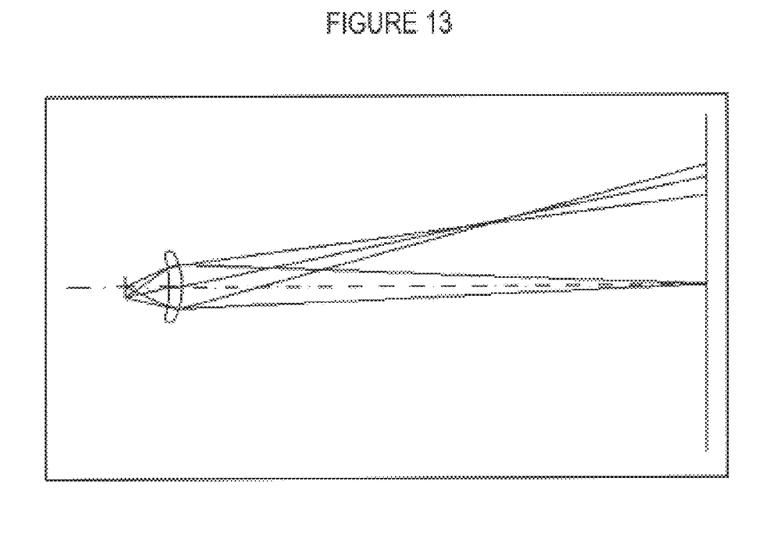
FIG. 13 shows array tracing of a typical germanium lens design suitable for an infrared endoscope, according to an embodiment of the invention.

FIG. 13 shows array tracing of a typical germanium lens design suitable for an infrared endoscope, according to an embodiment of the invention. Germanium is the usual material used to make IR-transmitting lenses. FIG. 13 shows the computed ray paths for a 0.8 mm square 16×16 array of 0.05 mm sized microbolometers, using a 2.5 mm diameter germanium lens with optical magnification of 10:1, giving a viewing area on the target of 8 mm×8 mm, with spatial resolution of 0.5×0.5 mm. Similar lens arrangements can be designed to give different magnifications, and to work with 32×32 arrays. Thus, an example of an array for an endoscope application would be a 32×32 array of 50 $\mu$m microbolometers. This array, complete with an IVP topcap, would be about 2.5 mm×2.5 mm. This is a possible optical arrangement of the endoscope: a small IVP 2D array is optically projected onto a larger target area by a magnifying germanium lens 2.5 mm in diameter. Optical magnification (i.e. the target area measured) may be varied by adjusting the distance of the lens from the 2D array. The computer ray tracing shown in FIG. 13 is for a 16×16 array of 50 $\mu$m sensors with 2.5 mm diameter germanium lens arranged to provide 10:1 magnification, allowing the array to view an area of 8×8 mm at the target with 0.5×0.5 mm resolution.

Figure 14:
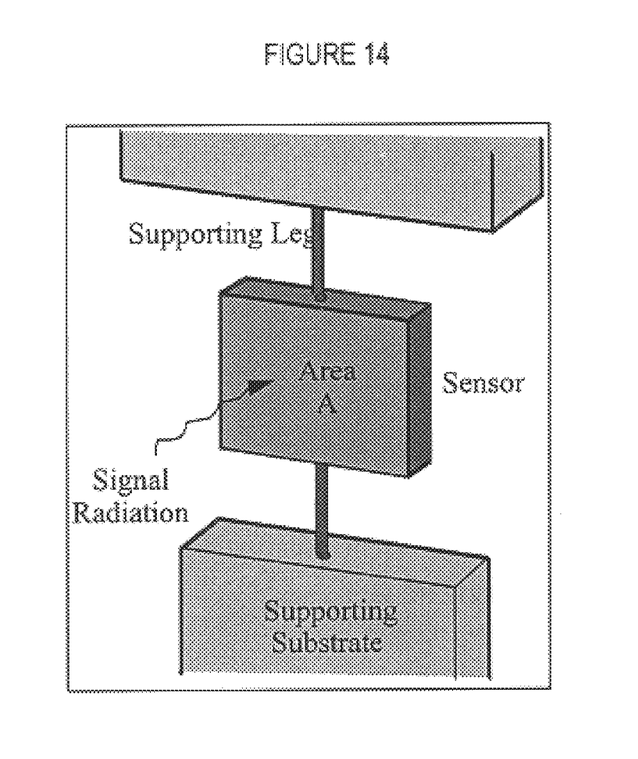
FIG. 14 shows an uncooled silicon IR thermal imaging sensor, according to an embodiment of the invention. The incident energy causes a local heating of the structure.
Figure 15:
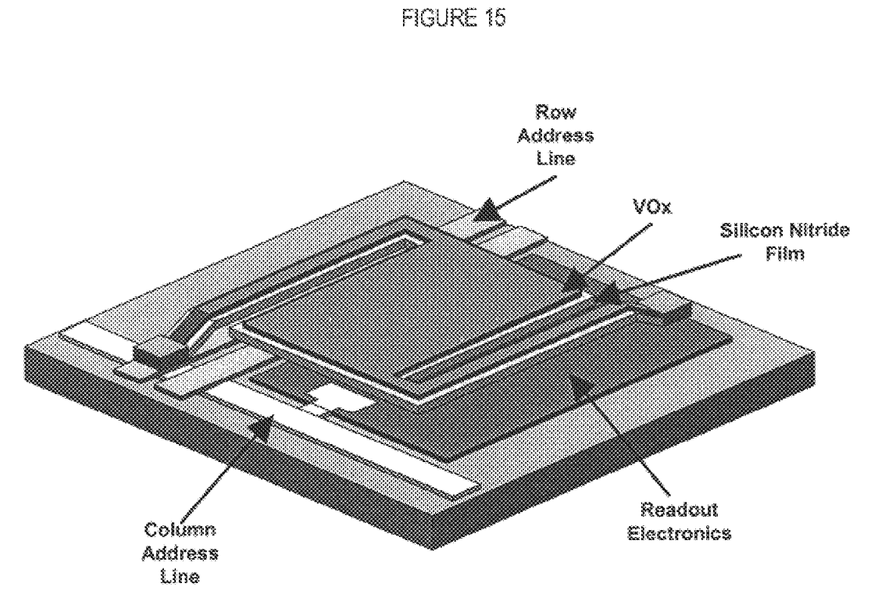
FIG. 15 shows features of the microbolometer sensor element, according to an embodiment of the invention.
Figure 16:
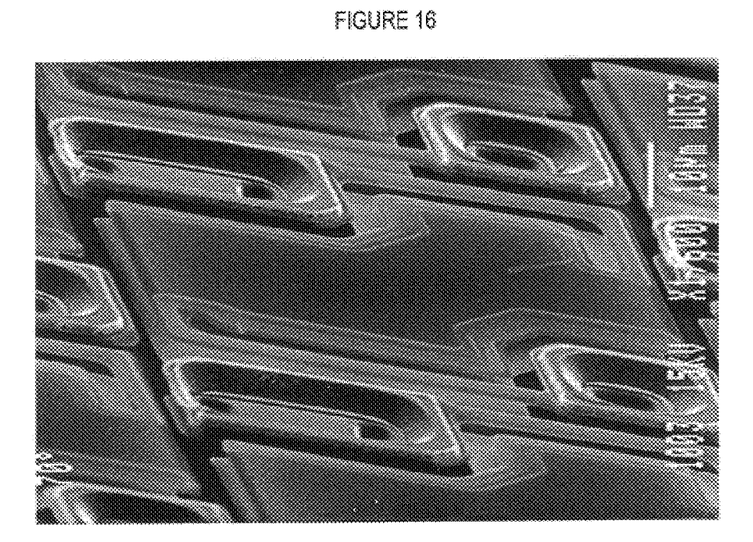
FIG. 16 shows an electron microscope photograph of part of a microbolometer array, according to an embodiment of the invention. Scale mark shows a 0.01 mm length.

FIG. 14 shows an uncooled silicon IR thermal imaging sensor, according to an embodiment of the invention. The incident energy causes a local heating of the structure. FIG. 15 shows features of the microbolometer sensor element, according to an embodiment of the invention. FIG. 16 shows an electron microscope photograph of part of a microbolometer array, according to an embodiment of the invention. Scale mark shows a 0.01 mm length.

Figure 17:
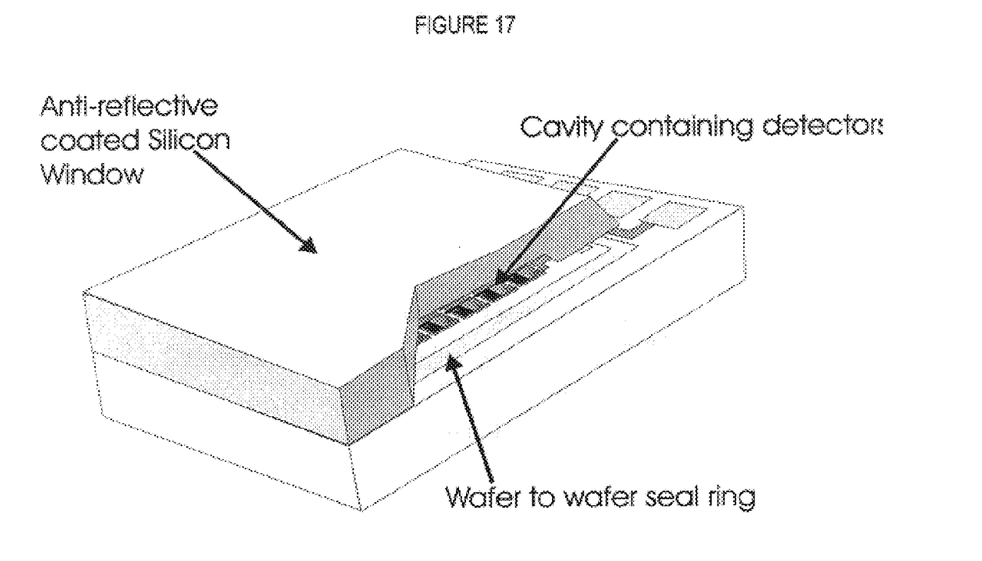
FIG. 17 shows a drawing of the construction of an integrated vacuum package with a two-dimensional array of uncooled IR sensors, according to an embodiment of the invention.
Figure 18:
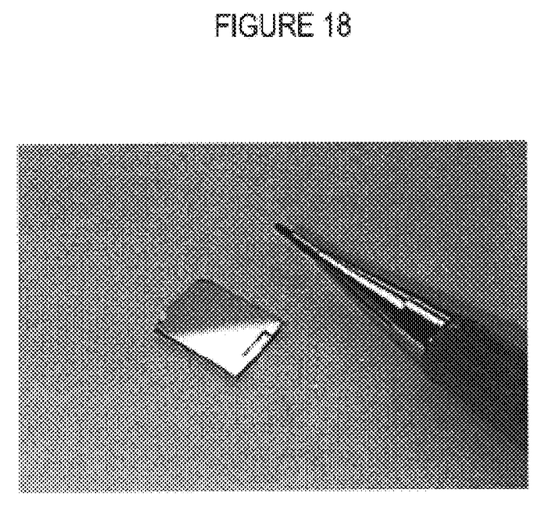
FIG. 18 shows a picture of a two-dimensional array of uncooled IR sensors with an integrated vacuum package, according to an embodiment of the invention.

FIG. 17 shows a drawing of the construction of an integrated vacuum package with a two-dimensional array of uncooled IR sensors, according to an embodiment of the invention. More specifically, FIG. 17 shows a coated silicon window bonded to an underlying silicon wafer to provide a vacuum cavity in which the infrared sensitive elements (detectors) operate. Finally, FIG. 18 shows a picture of a two-dimensional array of uncooled IR sensors with an integrated vacuum package, according to an embodiment of the invention, i.e. a picture of an integrated vacuum package on a two-dimensional microbolometer array.

Infrared techniques have advantages over other temperature measuring means including increased thermal accuracy, spatial accuracy, etc. An infrared sensitive endoscope is useful for other procedures beyond heat treatment including for example laparoscopic laser adhesiolysis, locating kidney stones in the ureter, identification of cancerous or precancerous lesions, looking for bowel perfusions, and locating blockages in the cardiovascular system.

In use, an infrared sensitive endoscope can be inserted through one small trocar made opening in the abdomen and manipulated to visualize almost any area to be thermally treated. A rigid endoscope would have value as well, but would not be able to access all treatment areas, even with multiple trocar made openings. Also, a rigid endoscope cannot be used effectively for treating body cavity surface diseases such as esophageal varices. The only present method to measure these temperatures is with MRI imaging. This is not only a very expensive procedure, thereby limiting the number of patients that could be helped, it uses RF emission from heat to measure tissue temperature. When using RF thermal treatments, temperature measurements have to be pulsed intermittently with RF treatment cessation in order to measure temperature.

Another potential method for measuring this temperature is to percutaneously place thermocouples of optic fibers in areas using ultrasound or fluroscopic guidance. However, with this method it is difficult to place the thermoprobes and the limited number of probes that can be practically placed limits spatial resolution. A surface IR measurement allows a continuum of temperature measurements in the field of view and can be observed simultaneously with direct vision. This can be invaluable during thermal treatments when attempting to spare vital tissues such a nerves, the diaphragm, adjacent organs, sphincters and other necessary and delicate tissues. The direct visual observation and temperature measurement would allow all of the thermal therapy treatments to become more effective because more power can be applied without concern for unknown temperature rises in adjacent vital tissues. The IR endoscope would also make the thermal treatment safer because the adjacent vital tissues can be directly observed for temperature changes.

While the invention has been described with reference to specific embodiments, the description is illustrative and is not to be construed as limiting the scope of the invention. Various other modifications and changes may occur to those skilled in the art without departing from the spirit and scope of the invention.

What is claimed is:

1. A thermal-imaging endoscope, comprising:
   an endoscope body having a distal end;
   an infrared microbolometer imaging device supported at the distal end of the endoscope body for providing thermal image data; and
   thermal image data communication apparatus, operably coupled with the infrared microbolometer imaging device, for communicating the thermal image data;
   wherein the infrared microbolometer imaging device is operably coupled with an integrated vacuum package at the distal end of the endoscope body.
2. The endoscope of claim 1, wherein the microbolometer imaging device comprises at least one array of imaging elements, the array having dimensions of N×M, where N and M are integers.
3. The endoscope of claim 2, wherein the at least one array is of varying grid density across its length and/or width.
4. The endoscope of claim 1, wherein the microbolometer imaging device comprises a circular array of imaging elements.
5. The endoscope of claim 1, wherein the microbolometer imaging device comprises an array of imaging elements in an irregular pattern to compensate for distortions caused by constraints on optics of the microbolometer imaging device.
6. The endoscope of claim 1, wherein the thermal image data communication apparatus comprises at least one optical fiber.
7. The endoscope of claim 1, further comprising a visual light imaging device supported at the distal end of the endoscope body for providing a visual light image.
8. The endoscope of claim 1, wherein the microbolometer imaging device is tilted with respect to a longitudinal axis of the endoscope body and with respect to a transverse axis of the endoscope body.
9. The endoscope of claim 1, wherein the endoscope body is constructed to be flexible along its length.
10. The endoscope of claim 1, further comprising apparatus for producing gas flow across a surface operably coupled with the microbolometer imaging device, to generally minimize condensation and/or contamination at said surface.
11. The endoscope of claim 1, wherein the microbolometer imaging device comprises micromachined, microscopic bridge structures constructed to quantify incident infrared radiation.
12. The endoscope of claim 1, wherein the integrated vacuum package is formed on the surface of the microbolometer imaging device.
13. The endoscope of claim 1, wherein the microbolometer imaging device is disposed within a vacuum-sealed capsule of the integrated vacuum package.
14. The endoscope of claim 1, wherein the microbolometer imaging device is made from silicon or GaAs material.
15. The endoscope of claim 1, wherein the microbolometer imaging device is angled with respect to longitudinal and transverse axes of the endoscope body.
16. The endoscope of claim 1, wherein the endoscope body is flexible along generally its entire length.
17. The endoscope of claim 1, wherein the microbolometer imaging device comprises an array of imaging elements, the array being disposed in a plane that is tilted with respect to a longitudinal axis of the endoscope body and with respect to a transverse axis of the endoscope body.
18. The endoscope of claim 1, wherein the microbolometer imaging device is adapted to detect radiation in the 2 to 14 μm wavelength band.
19. The endoscope of claim 1, further comprising apparatus for creating a multi-dimensional thermal image map using the thermal image data.
20. The endoscope of claim 19, further comprising a visual imaging device at the distal end of the endoscope body, and apparatus for superimposing the thermal image map and a visual image from the visual imaging device relative to each other.
21. The endoscope of claim 1, further comprising apparatus for providing gas flow across a surface operably coupled with the imaging device to generally minimize condensation and/or contamination at said surface.

* * * * *